(12) United States Patent
Bartko et al.

(10) Patent No.: US 10,598,576 B2
(45) Date of Patent: Mar. 24, 2020

(54) PARTICLE SAMPLE PREPARATION WITH FILTRATION

(71) Applicant: BATTELLE MEMORIAL INSTITUTE, Columbus, OH (US)

(72) Inventors: Andrew P. Bartko, Worthington, OH (US); Theodore J. Ronningen, Lewis Center, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 16/545,675

(22) Filed: Aug. 20, 2019

(65) Prior Publication Data

US 2020/0064240 A1 Feb. 27, 2020

Related U.S. Application Data

(60) Provisional application No. 62/720,267, filed on Aug. 21, 2018.

(51) Int. Cl.
*G01N 1/40* (2006.01)
*G01N 1/14* (2006.01)

(52) U.S. Cl.
CPC .............. *G01N 1/4077* (2013.01); *G01N 1/14* (2013.01); *G01N 2001/149* (2013.01); *G01N 2001/4088* (2013.01)

(58) Field of Classification Search
CPC .................. G01N 1/4077; G01N 1/14; G01N 2001/4088; G01N 2001/149
See application file for complete search history.

(56) References Cited

U.S. PATENT DOCUMENTS

| 4,142,668 A | * | 3/1979 | Lee | ........................ | B01L 3/5021 |
| | | | | | 210/131 |
| 4,454,235 A | * | 6/1984 | Johnson | .................. | B01L 3/021 |
| | | | | | 422/68.1 |
| 2004/0136497 A1 | | 7/2004 | Meldrum et al. | | |

FOREIGN PATENT DOCUMENTS

| WO | 2010/107399 A1 | 9/2010 |
| WO | 2012/012172 A2 | 1/2012 |
| WO | 2017/105625 A1 | 6/2017 |

OTHER PUBLICATIONS

Notification of Transmittal with the International Search Report and the Written Opinion of the International Searching Authority for PCT International Application No. PCT/US2019/047226; European Patent Office; Rijswijk, The Netherlands; dated Nov. 25, 2019.

* cited by examiner

*Primary Examiner* — David Z Huang
(74) *Attorney, Agent, or Firm* — Thomas E. Lees, LLC

(57) ABSTRACT

A liquid transfer line receives a liquid having particles suspended therein and transfers the liquid to a capillary tube. A support tube secures the capillary tube therein. The support tube is substantially airtight except at a designated position. An optional securement secures the capillary tube within the support tube. A discharge end of the capillary tube is spaced from, and receded into, a discharge end of the support tube. A chuck is positioned below the support tube and is operable to open and to close to seal the designated position of the support tube. A sample substrate filters the liquid introduced through the liquid transfer line. Yet further, the sample preparation system comprises a pump that draws a vacuum that exhausts portions of the liquid that are not retained on the sample substrate.

20 Claims, 5 Drawing Sheets

PARTICLE SAMPLE PREPARATION WITH FILTRATION

CROSS REFERENCE TO RELATED APPLICATIONS

This application claims the benefit of U.S. Provisional Patent Application Ser. No. 62/720,267, filed Aug. 21, 2018, entitled PARTICLE SAMPLE PREPARATION WITH FILTRATION, the disclosure of which is hereby incorporated by referenced.

BACKGROUND

Various aspects of the present disclosure relate generally to particle sample preparation and in particular to the separation of suspended, microscopic particles from a liquid source for subsequent analysis.

The monitoring of particulate matter has received an increasing amount of attention in recent years because of the potential impact of particulates on radiative and climatic processes, on contamination of products, on human health and because of the role particles play in atmospheric transport and deposition of pollutants. As an illustration, it may be desirable to detect the presence of particulates in the air, in water supplies or on persons. It may also be desirable to detect the presence of particulates on materials that may be found in semiconductor clean rooms, pharmaceutical production facilities and biotechnology laboratories to verify that there has been no contamination produced in such environments that would create undesirable environmental exposures or adversely affect manufacturing, testing or experimental processes.

As another illustration, it may be desirable to analyze the air in a predetermined location for particulates that fall within a range of sizes that can be inhaled, such as naturally occurring or artificially produced airborne pathogens, allergens, bacteria, viruses, fungi and biological or chemical agents that are found in or are otherwise introduced into the location. For example, the ability to detect the presence of particular airborne particulates in hospitals, nursing homes, rehabilitation centers and other care facilities may be beneficial to assist in preventing the spread of disease, infection or harmful bacteria.

BRIEF SUMMARY

According to aspects of the present disclosure a sample preparation system is provided. The sample preparation system comprises a capillary tube having a discharge end, and a liquid transfer line that terminates into the capillary tube. Under this configuration, the liquid transfer line receives a liquid having particles suspended therein and transfers the liquid to the capillary tube. The sample preparation system also comprises a support tube that is positioned about the capillary tube such that a discharge end of the capillary tube is spaced from and receded into a discharge end of the support tube. By way of example, the support tube may be airtight except at a designated position, e.g., at or about an end thereof. Also, the sample preparation system comprises a sample substrate positionable adjacent to the support tube. The sample substrate receives the liquid discharged from the capillary tube and filters the suspended particles from the liquid. The sample preparation system still further comprises a chuck interposed between a support member and the sample substrate. The chuck is operable to open and close, thereby selectively creating a seal between the sample substrate and the support tube. The sample preparation system moreover comprises a pump that draws the liquid through the sample substrate.

The sample preparation system may optionally comprise a securement that secures the capillary tube within the support tube. In other example embodiments, the capillary tube is constructed from the support tube, e.g., by drilling the capillary tube into the support tube.

According to further aspects of the present disclosure, a process for preparing a sample using a sample preparation system is provided. The process comprises receiving a liquid at a liquid transfer line, where the liquid comprises suspended particles. The process further comprises opening a chuck and inserting a sample substrate between the chuck and the liquid transfer line. In this process, the sample substrate comprises a surface that is directed towards the liquid transfer line. The process still further comprises closing the chuck and drawing the liquid from the liquid transfer line through a capillary tube. Here, the capillary tube is located within a support tube. The method moreover comprises drawing the liquid through the sample substrate such that particles are trapped on the surface of the sample substrate.

According to still further aspects of the present disclosure, a sample preparation system is provided. The sample preparation system comprises a capillary tube having a discharge end and an opening. The opening has a length and a width such that the width is orthogonal to the length, and the length is greater than the width. A liquid transfer line terminates into the capillary tube, such that the liquid transfer line receives a liquid comprising suspended particles and transfers the received liquid to the capillary tube. Moreover, a support tube having a discharge end, is positioned about the capillary tube such that the discharge end of the capillary tube is spaced from and receded into the discharge end of the support tube. A securement secures the capillary tube within the support tube such that the support tube is airtight except at a designated position. Also, a sample substrate is positionable adjacent to the support tube. The sample substrate receives the liquid discharged from the capillary tube and filters the suspended particles from the liquid. Still further, a chuck is interposed between a support member and the sample substrate. The chuck is operable to open and close, thereby selectively creating a seal between the sample substrate and the support tube. A pump draws the liquid through the sample substrate and that exhausts portions of the liquid that are not retained on the sample substrate.

DETAILED DESCRIPTION

Various aspects of the present disclosure provide systems and processes for the separation of suspended, microscopic particles from a liquid source. In example embodiments, the separated particles are collected onto a solid substrate for subsequent analysis. As will be described in greater detail herein, in some embodiments, a capillary tube facilitates the deposition of a liquid onto a solid sample substrate (e.g., such as a thin film, porous substrate, which may be coated to match the needs of subsequent, optical analysis of the particles). The liquid is drawn through pores of the sample substrate such that particles are left on a surface of the substrate. As such, particulates are separated from the corresponding liquid source. Moreover, the particles are confined to a limited region of the sample substrate by designing and positioning the capillary tube to limit the area where the liquid passes through the sample substrate.

In practical implementations, the sample preparation system herein can be used to separate microscopic particles (e.g., size range of 0.1 micrometer ($\mu$m) diameter and greater) from a liquid that the particles are suspended in. The particles are intended to be optically analyzed after separation. Accordingly, the sample substrate that the particles are collected on can have characteristics that support the associated subsequent analysis requirements. In addition, the sample preparation system herein provides a collected sample that is beneficial for subsequent analysis by confining the particles to a limited region of the sample substrate, thus reducing the burden of the subsequent analysis equipment to analyze the collected sample.

Figure 1:
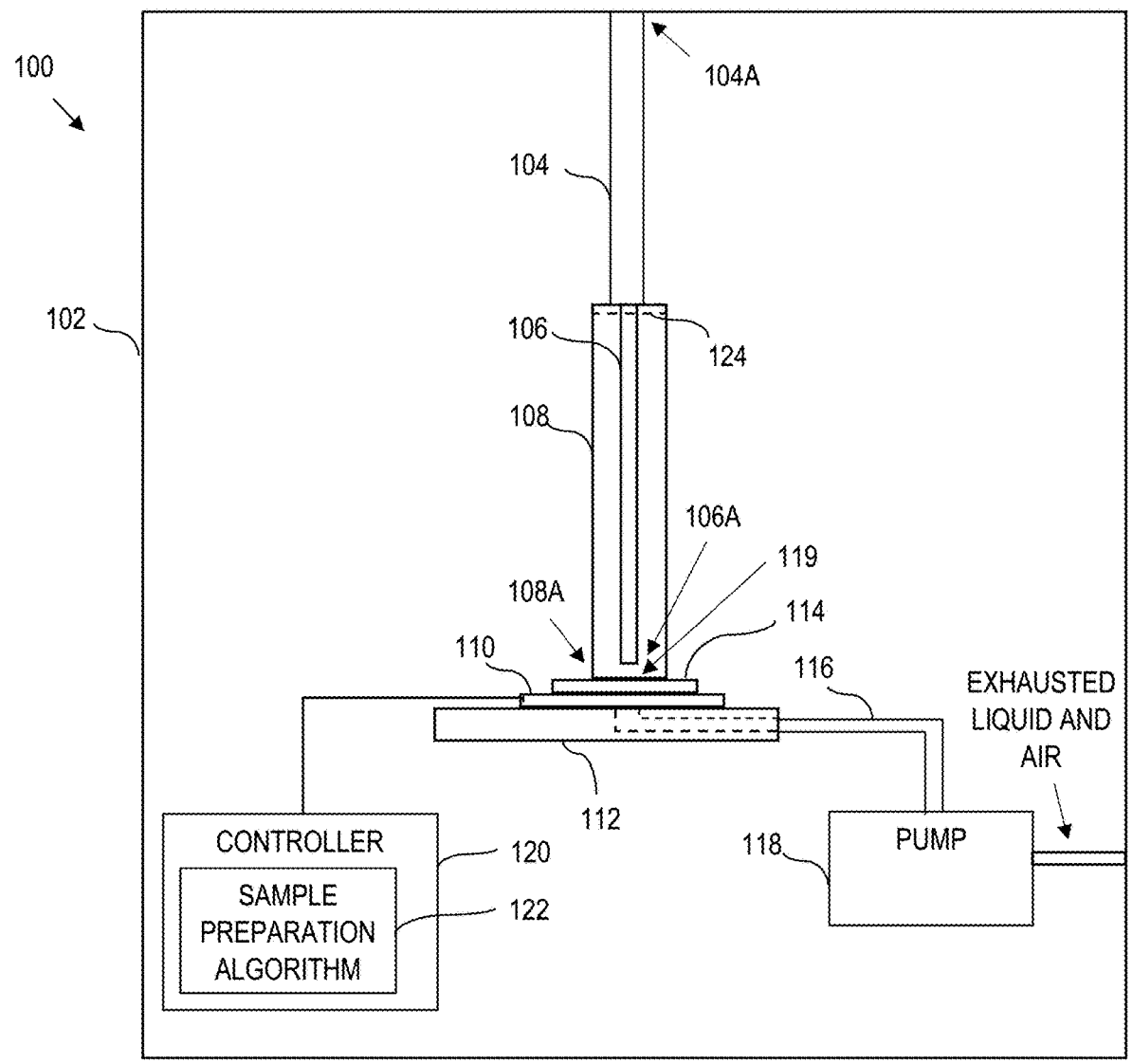
FIG. 1 is a block diagram of a sample preparation system according to aspects of the present disclosure.

Referring now to the drawings, and in particular to FIG. 1, a sample preparation system 100 is illustrated according to aspects of the present disclosure. The sample preparation system 100 is schematically illustrated to include a housing 102 defining a collector. The housing 102 can comprise any suitable structure as the specific application dictates. In other applications, a housing 102 is not strictly required, such as where the below-described components are assembled in an integrated manner.

Within the housing 102, the sample preparation system 100 comprises a liquid transfer line 104, a capillary tube 106, and a support tube 108. The sample preparation system 100 also comprises a moveable chuck 110 and an optional support member 112. Also as illustrated, a sample substrate 114 can be inserted and removed, fed, advanced, or otherwise selectively positioned and adjusted within the housing 102. For instance, as illustrated, the chuck 110 is situated between the support member 112 and a sample substrate 114 that has been inserted therein. Ductwork 116 extends through the support member 112 and couples to a pump 118. The sample preparation system 100 can also optionally comprise a controller 120 and corresponding sample preparation algorithm 122.

As illustrated, the liquid transfer line 104 provides an inlet 104A to introduce a liquid containing suspended particulates into the collector. The liquid transfer line 104 extends into the housing 102 and terminates into the capillary tube 106. Thus, in example implementations, the liquid transfer line 104 receives a liquid comprising suspended particles and transfers the received liquid to the capillary tube 106. In practical applications, the material(s) of construction for the liquid transfer line 104 can be selected to inhibit biological binding to an inside diameter of the liquid transfer line 104.

The capillary tube 106 accepts from the liquid transfer line 104, a liquid that was introduced therein. Moreover, the capillary tube 106 serves as a conduit to move the liquid from the liquid transfer line 104 towards the sample substrate 114. As such, in some embodiments, a passageway through the liquid transfer line aligns with (e.g., is coaxial with), a passageway through the capillary tube 106. The capillary tube 106 includes a discharge end 106A, e.g., illustrated as a capillary opening at the bottom of the capillary tube 106 opposite the inlet 104A. As will be described in greater detail herein, in example embodiments, the capillary tube 106 can have an opening at the discharge end 106A that is narrow in one dimension (tens of microns to a few millimeters) and extended in the other dimension (several to tens of millimeters).

The capillary tube 106 is constructed of a material that is non-reactive with the liquid processed by the collector and is further non-reactive with the particles collected by the collector. Moreover, in certain embodiments, a length of the capillary tube 106 is minimized to lower the probability of biological particle binding.

The support tube 108 supports the capillary tube 106 and also includes a discharge end 108A, which is illustrated in FIG. 1 as a bottom side of the support tube 108. The support tube 108 can be constructed of any suitable material that may be dictated by the particular use of the collector. As will be described more fully herein, the capillary tube 106 is secured inside of the support tube 108 such that the support tube 108 is airtight (e.g., relative to the capillary tube 106) except for its bottom side. The capillary tube 106 passes through the support tube 108 and is securely positioned and sealed in place, either permanently or using a removable fixture.

During sample collection (e.g., during sample injection into the liquid transfer line 104), a seal is formed about the bottom of the support tube 108. The seal allows for the pressure inside the support tube 108 to be reduced, and a pressure differential draws liquid down the capillary tube 106.

As illustrated, the capillary tube 106 is positioned inside of and/or contained within the support tube 108. More particularly, the support tube 108 is positioned about the capillary tube 106 such that the discharge end 106A (e.g., capillary opening) of the capillary tube 106 is spaced from, and receded into the discharge end 108A (e.g., illustrated as a bottom side) of the support tube 108. The distance that the capillary opening 106A is spaced from the bottom side 108A of the support tube 108 can be set, fixed, adjustable/tunable, calibratable, etc., to achieve a desired sample collection size by affecting a discharge point of the liquid relative to the sample substrate 114. For instance, in some embodiments, the spread of the liquid on the sample substrate 114 during sample filtration/sample collection can be limited, e.g., to the area defined by the capillary opening 106A. Moreover, the distance from the capillary opening 106A to the sample substrate 114, and the cross-sectional area of the capillary opening 106A are thus process parameters that can manipulated to control the size/area of the collected sample on the sample substrate 114.

As will be described more fully herein, In an example configuration, the capillary tube 106 is secured and positioned via the support tube 108 such that the discharge area 106A (i.e., capillary opening) is within a few microns to a millimeter from the sample substrate 114. In this way, the spread of the liquid on the sample substrate 114 is limited to the area defined by the capillary opening. In practical embodiments, the filtered particles deposit in an area that mirrors the shape of the capillary opening.

In some embodiments, the support tube 108 is airtight except at a designated position. In the illustrated configuration, the designated position comprises the discharge end, i.e., the bottom side 108A of the support tube 108 in the illustrated example.

In some embodiments, the capillary tube 106 passes through this support tube 108 and is securely positioned and sealed in place via an optional securement 124. Here the securement can secure the capillary tube 106 within the support tube 108. In practical applications the securement secures the capillary tube 106 within the support tube 108, wherein the support tube 108 is airtight except at a designated position (e.g., an area of the sample substrate 114 in register with the discharge end 108A of the support tube.

As a few examples, the securement 124 can secure the capillary tube 106 within the support tube 108 permanently, e.g., via friction or compression fitting, permanent molding, etc. The capillary tube 106 can also be formed integral in the support tube 108, such as through drilling, machining, additive manufacturing, etc. In other embodiments, the securement can secure the capillary tube 106 to the support tube 108 using a removeable fixture, such as one or more clamps, retaining rings, or other fixtures (not shown in FIG. 1) for sake of clarity.

In some embodiments, the liquid transfer line 104 can be formed integral with the capillary tube 106, the support tube 108, or both, e.g., via drilling, machining, additive manufacturing, etc. In other embodiments, friction, compression fitting, permanent molding, clamps, retaining rings, or other fixtures can be used to couple the liquid transfer line 104 to the capillary tube 106 and/or the support tube 108.

In the illustrated embodiment, the moveable chuck 110 is positioned below the support tube 108, e.g., interposed between the support member 112 and the sample substrate 114. However, other chuck configurations could alternatively be used. For instance, the chuck 110 can be mounted on the support member 112. Regardless, the moveable chuck 110 is operable to open and to close, thereby selectively creating a seal between the sample substrate 114 and the support tube 108. When the chuck 110 is closed, the chuck 110 also forms a seal proximate a designated position (e.g., discharge area 108A, e.g., bottom side) of the support tube 108, as described more fully herein. As such, the chuck 110 closes when a vacuum will be drawn. The chuck 110 opens, e.g., when the sample of collected particles needs to be removed, advanced, or otherwise adjusted.

The support member 112 can be implemented as a plate, support station, etc. In this regard, the support member 112 forms part of the structure of the collector and provides a means for extending ductwork, containing control electronics, etc.

In some embodiments, the sample substrate 114 is positionable adjacent to the support tube 108, e.g., between the chuck 110 and the support tube 108. The sample substrate 114 receives the liquid discharged from the capillary tube 106 and filters the suspended particles from the liquid (e.g., filters the liquid introduced through the liquid transfer line 104). In an example implementation, the sample substrate 114 comprises a thin film, porous substrate that acts as filter. The pores in the filter defined by the sample substrate 114 are large enough to allow the movement of air and liquid therethrough. The pores are small enough that targeted particles remain on the top surface of the sample substrate 114. Thus, the sample substrate 114 can comprise a porous filter that prohibits targeted particles from passing through the porous filter, where the porous filter further permits passage of liquid and air through the porous filter.

In an example embodiment, the sample substrate 114 is sufficiently flexible and pliable to not hinder a vacuum seal between the chuck 110 and the support tube 108.

Moreover, in an example embodiment, the sample substrate 114 is selected and/or configured to allow reliable spatial registration of the collected particles relative to the subsequent analysis. In this regard, the sample substrate includes a registration feature that allows registration of the sample substrate relative to the capillary tube 106. For instance, in an example implementation, the sample substrate 114 can be easily punctured (puncturable) to create a registration feature(s) that are used to position the substrate and collected particles for subsequent optical analysis.

In an example embodiment, the sample substrate 114 has a surface coating that is selected to support optical analysis. The particles are collected on this coated surface. In an example implementation, the surface coating of the sample substrate 114 comprises a metallic coating that is optically reflective and does not contribute to a measured optical spectrum. For instance, an example metallic coating can enable a surface that is optically reflective and does not contribute to a measured optical spectrum (e.g., Raman, fluorescence, reflectance). The surface coating should also be selected to ensure that the sample substrate 114 does not degrade or modify the particles collected thereon. Thus, in this example, the sample substrate 114 comprises a surface coating that collects particles of interest thereon, where the particles of interest measurable on an optical spectrum.

For instance, the sample substrate 114 can include a Raman silent biological capture material. Thus, the sample substrate 114 does not contribute to the measured spectra of the organism that it supports. As an example illustration, the sample substrate can comprise a glass layer (e.g., borosilicate or similar glass material) that also defines a base layer, having an aluminum layer over the glass layer. Preferably, the flatness and roughness of the glass layer should not exceed λ/10 and 60-40 scratch-dig.

In addition to the above, the Raman silent substrate can include one or more biologically compatible material layers that are over the aluminum layer to provide desired functionality. For example, the biologically compatible material layer can include Poly-l-lysine and Agarose. Moreover, Agarose can be modified to provide differing degrees of resilience (i.e. spongy or rubbery) to suit a desired application. The resilience can be modified, for example, by changing the amount of water in the Agarose.

As illustrated, the ductwork 116 can extend through the support member 112. Moreover, the ductwork 116 can couple to a pump 118 that draws the liquid through the sample substrate. The ductwork 116 can also provide other pathways, e.g., to exhaust the liquid, air, etc. In this regard, necessary valves, fittings, control flows, etc., can be provided as needed by the specific implementation.

In use, the liquid transfer line 104 receives a liquid having particles suspended therein. For instance, the liquid can be supplied manually or automatically via a syringe or other delivery mechanism. Moreover, the particles of interest that are to be separated can include any microscopic particles that remain suspended in a liquid. Example particles of interest include cellular material, such as bacteria, fungi, or eukaryotic, etc. Also, the liquid could be a pure chemical or a solution. Moreover, certain embodiments accommodate a variety of liquids, with varying chemical composition, viscosity, pH and reactivity. Regardless, the liquid transfer line 104 transfers the liquid to the capillary tube 106.

More particularly, the chuck 110 is initially open. A desired sample area 119 of the sample substrate 114 is introduced in register with the discharge end 106A of the capillary tube 106. Also as illustrated, an end of the ductwork 116 aligns in register with the discharge end 106A of the capillary tube 106, and hence, the desired sample area 119. For instance, a sample substrate 114 can be inserted into the sample preparation system, e.g., positioned between the bottom 108A of the support tube 108 and the chuck 110. In another example, the sample substrate 114 can be advanced such that a new area of a film body of the sample substrate 114 is designated as the desired sample area 119. The designated position (e.g., the bottom side 108A of the support tube 108) is sealed, such as by closing the chuck 110 to draw the substrate 114 into sealed relationship with the support tube 108. Once the designated position (e.g., bottom side 108A) of the support tube 108 is sealed, the sample can be injected into the liquid transfer line 104. The sealing of the support tube 108 during sample injection, allows for pressure inside the support tube 108 to be reduced relative to pressure in the liquid transfer line 104, and the pressure differential draws liquid down the capillary tube 106.

The chuck 110 can be manually operable, or the chuck 110 can be integrated into an automated machine, e.g., using a motor to open and close the chuck 110 under computer control, e.g., via the controller 120 executing the sample preparation algorithm 122.

The pump 118 draws a vacuum via ductwork 116 (which can run through the support member 112). The vacuum draws the liquid from liquid transfer line 104 into the capillary tube 106 and from the capillary tube 106 through the sample substrate 114. Here, solid particles are collected on the surface of the sample substrate 114, and the liquid and air passes through the sample substrate 114. The liquid and air that pass through the filter of the sample substrate 114 are drawn through the ductwork 116 and can be exhausted from the system, reclaimed, discarded, etc.

For instance, as noted more fully herein, the sample substrate defines a filter having pores that are dimensioned larger than liquid and air moving therethrough, the pores also being dimensioned small enough that targeted particles remain on a top surface of the sample substrate. As such, the liquid is drawn through pores of the substrate 114 such that the particles are left on the surface of the substrate 114. Moreover, as noted more fully herein, the particles are confined to a limited region of the substrate 114 by designing and positioning the capillary tube 106 to limit the area where the liquid passes through the substrate 114.

In an example configuration, the separate microscopic particles (size range of 0.1 um diameter and greater) are thus separated from a liquid that the collected particles were suspended in. The particles are intended to be optically analyzed after separation, so the sample substrate 114 that the particles are collected on should have characteristics that support that analysis. In addition, it is beneficial for subsequent analysis to confine the particles to a limited region of the substrate 114, as disclosed more fully herein.

After drawing sufficient liquid to collect a suitable sample, the pump 118 can be stopped thereby relieving the vacuum. This allows the chuck 110 to be re-opened, thus allowing the sample substrate 114 to be removed, advanced, adjusted, repositioned, etc. from the system for subsequent analysis. Removal of the sample substrate 114 can occur manually or using an automated means.

For instance, in an example configuration, once a desired volume of liquid has been drawn through the capillary tube 106 and the sample substrate 114, the vacuum created via the pump 118 is removed and the chuck 110 is opened. The sample substrate 114 is then removed, either manually or automatically, from the collector housing 102 and can be positioned for analysis, sample storage, sample conditioning/processing, etc., e.g., via the controller 120 executing the sample preparation algorithm 122.

In another example configuration, the capillary tube 106 is secured and positioned within the support tube 108 such that the capillary opening 106A of the capillary tube 106 opposite the liquid transfer tube 104 is within a few microns to a millimeter from the sample substrate 114 when the sample substrate 114 is installed between the chuck 110 and the support tube 108. In this way, the spread of the liquid on the sample substrate 114 during sample filtration/sample collection is limited to the area defined by the capillary opening 106A. For instance, the filtered particles can deposit in an area that mirrors the shape of the capillary opening 106A.

Figure 2:
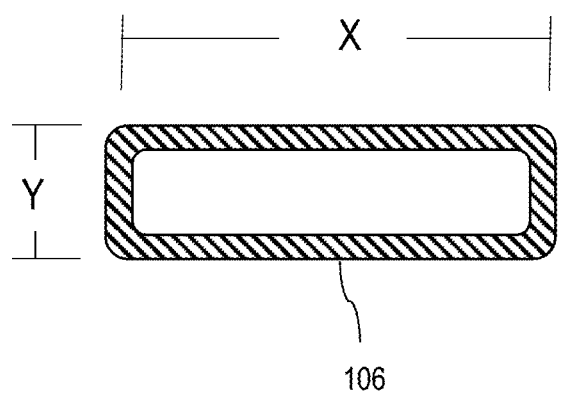
FIG. 2 is a schematic diagram of an example cross section of a capillary tube usable with the sample preparation system of FIG. 1.

Referring to FIG. 2, in an example configuration, the capillary tube 106 has an opening that is narrow in one dimension (e.g., the 'Y' dimension as schematically illustrated), and extended in an orthogonal dimension (e.g., the 'X' dimension as schematically illustrated). For instance, in an example implementation, the capillary tube 106 comprises a capillary opening 106A having a length that is greater than a corresponding width, wherein the width extends in a dimension that is orthogonal to the length. As more specific examples, in an embodiment, the length is greater than one (1) millimeter (mm). In yet another embodiment, the corresponding width is between one (1) micrometer ($\mu$m) and one (1) millimeter (mm).

In yet further examples, a cross section of the capillary tube 106 is tens of microns to a few millimeters in the Y dimension. In another example implementation, the cross section of the capillary tube is extended in the 'X' dimension several to tens of millimeters. In yet another example implementation, the cross section of the capillary tube 106 is tens of microns to a few millimeters in the Y dimension and several to tens of millimeters in the 'X' dimension.

Figure 3:
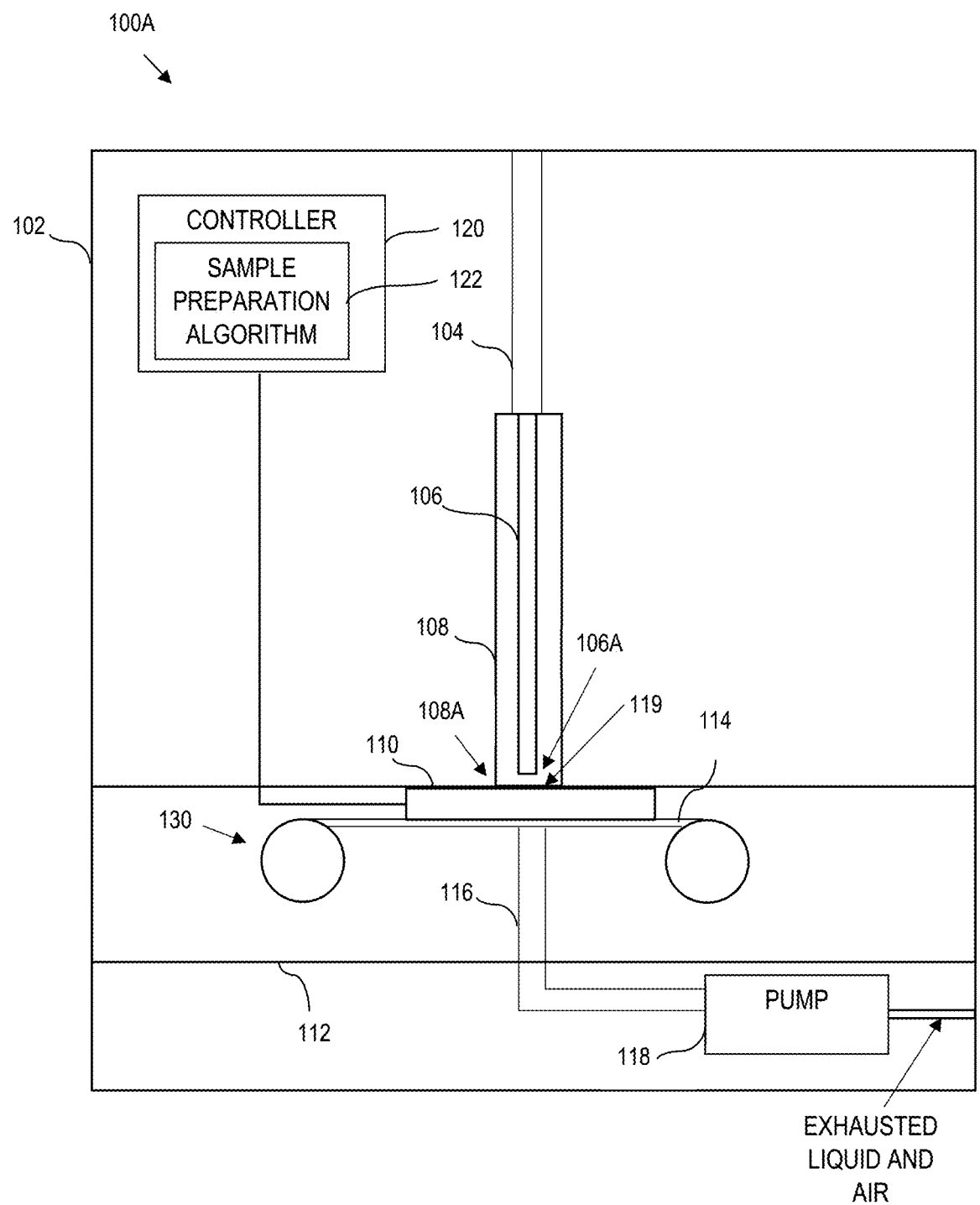
FIG. 3 is a block diagram of a sample preparation system according to further aspects of the present disclosure.

Referring to FIG. 3, a sample preparation system is illustrated according to further aspects of the present disclosure. The sample preparation system 100A can include all of the features, components, capabilities, etc., as described above with reference to FIG. 1 and FIG. 2. As such, like structure is illustrated with like reference numerals. Accordingly, the discussion of analogous features is not repeated herein. The sample preparation system 100A of FIG. 3 differs from the sample preparation system 100 of FIG. 1 in the configuration of the sample substrate 114. The sample preparation system 100 of FIG. 1 is sized to support a single sample substrate 114 at a time. The sample substrate 114 may be moved, repositioned, etc. However, the sample substrate 114 fits within the chuck 110.

In example embodiments, the sample substrate 114 comprises a strip of material that provides for multiple, discrete, and individual sample collection sites, e.g., for multiple sample collection sites to be discretely and individually collected. For instance, the sample preparation system 100A of FIG. 3 implements the sample substrate 114 as part of a strip or roll of material 130 such that a portion of the strip is used for each collected successive sample. This allows the strip to be advanced until the strip is full. The entire strip can then be extracted from the system 100A for subsequent analysis.

Referring to FIG. 3 in a manner analogous to that set out in FIG. 1, a sample preparation system comprises a housing 102. Within the housing 102, the sample preparation system comprises a liquid transfer line 104 that receives a liquid having particles suspended therein and transfers the received liquid to a capillary tube 106. A support tube 108 contains the capillary tube 106 therein such that a discharge end 106A of the capillary tube is spaced from and is receded into a discharge end 108A of the support tube 108.

The sample preparation system can also comprise a chuck 110. In the embodiment of FIG. 1, the chuck 110 is positioned between the support member 112 and the sample substrate 14. However, in the embodiment of FIG. 3, the chuck 110 is positioned below the support tube 108 (or between the support tube 108 and the sample substrate 114). Analogous to the embodiment of FIG. 1, the sample substrate 114 filters the liquid introduced through the liquid transfer line 104. Here, the support member 112 is below the sample substrate 114.

Notably, the chuck 110 is operable to open, and to close thus sealing the designated position of the support tube 108. Moreover, the sample preparation system can comprise ductwork 116 that passes through the support member 112, and couples an area in-line/in register with the discharge end 106A of the capillary tube 106 just below the sample area 119 of the sample substrate 114, to a pump 118 that exhausts portions of the liquid that are not retained on the sample substrate. Also, analogous to FIG. 1, the sample preparation system comprises a controller 120 executing a sample preparation algorithm 122 (e.g., the algorithm of FIG. 4 and/or FIG. 5).

In this regard, the chuck 110 may be between the support tube 108 and the sample substrate 114, or the sample substrate 114 can be positioned between the support tube 108 and the chuck 110 and/or support member 112, depending upon the specific configuration. Regardless, the support tube 108, amount of recess of the discharge end 106A of the capillary tube 106, and the sample substrate 114 cooperate to define the sample collection area.

Figure 4:
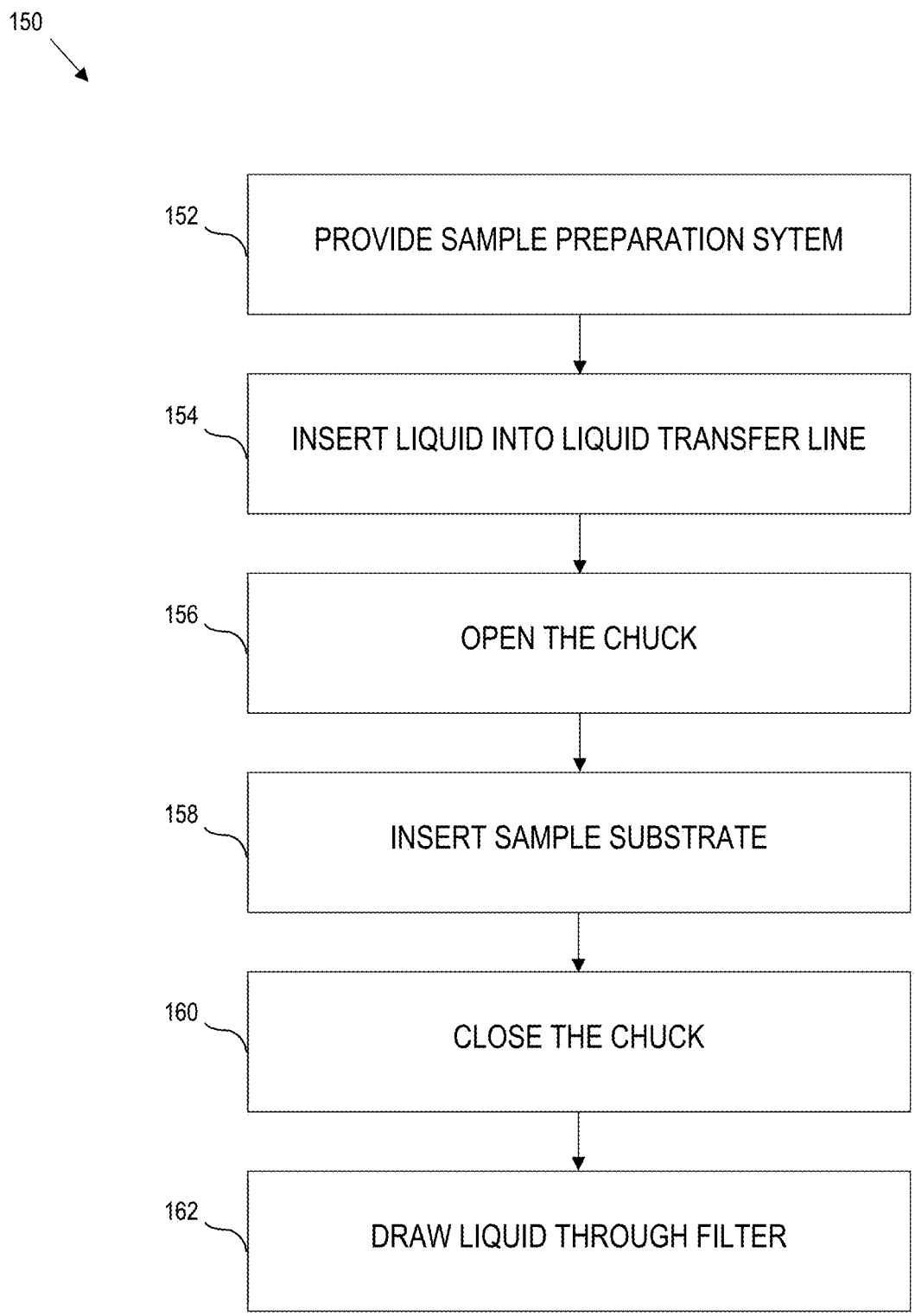
FIG. 4 is a flow chart of a process for preparing a sample according to aspects of the present disclosure.

Referring to FIG. 4, a process 150 is illustrated for preparing a sample. The process 150 comprises providing at 152 a sample preparation system. The sample preparation system can comprise any one or more of the features and components as described with reference to the sample preparation system 100 of FIG. 1 and FIG. 2, the sample preparation system 100A of FIG. 3, or a combination thereof.

For instance, the sample preparation system can comprise a capillary tube, a liquid transfer line that terminates into the capillary tube, wherein the liquid transfer line receives a liquid having particles suspended therein and transfers the liquid to the capillary tube. The sample preparation system can also comprise a support tube that is positioned about the capillary tube such that a discharge end of the capillary tube is spaced from and receded into a discharge end of the support tube. In some embodiments, the support tube secures the capillary tube therein. Moreover, the support tube can be airtight except at a designated position. The sample preparation system can also include an optional securement that secures the capillary tube within the support tube such that the discharge end of the capillary tube is spaced from and receded into the discharge end of the support tube. Yet further, the sample preparation system comprises a chuck (e.g., optionally positioned below the support tube), the chuck operable to open and to close to seal the designated position of the support tube. The sample preparation system can further comprise a sample substrate (e.g., positionable between the chuck and the support tube, or otherwise positioned) to filter a liquid introduced through the liquid transfer line, and a pump that draws a vacuum that exhausts portions of the liquid that are not retained on the sample substrate.

The process also carries out a procedure that can be controlled, for instance, e.g., via the controller 120 executing the sample preparation algorithm 122 (FIG. 1 or FIG. 3).

The process 150 comprises inserting, at 154, the liquid having particles suspended therein into the liquid transfer line. In some embodiments, inserting at 154 is satisfied by enabling a user to manually insert the liquid, queueing the system to wait for and expect a liquid, providing an instruction to insert, interacting with an external automated injection mechanism, combinations thereof, etc.

The process 150 also comprises opening, at 156, the chuck.

The process 150 further comprises inserting, at 158, the sample substrate into the sample preparation system, e.g., by inserting a sample substrate between the chuck and the support tube, advancing a film, etc., as described more fully herein, opening a feature for manual loading, interacting with an automated loader, combination thereof, etc.

The process 150 yet further comprises closing, at 160, the chuck.

The process also comprises operating, at 162, the pump to draw a vacuum so as to draw the liquid from the liquid transfer line through the capillary tube and through the filter of the sample substrate such that particles are trapped on a surface of the substrate.

Once the desired volume of liquid has been drawn through the capillary and the filter, e.g., as determined by the controller 120 based upon pre-programmed limits, amount of sample buildup, time, etc., the vacuum is removed and the chuck is opened. The substrate is then removed, either manually or automatically, from the collector and can be positioned for analysis.

In illustrative embodiments, the process 150 is carried out in sequential order as described above. In other embodiments, one or more processing steps may be implemented out of order.

Figure 5:
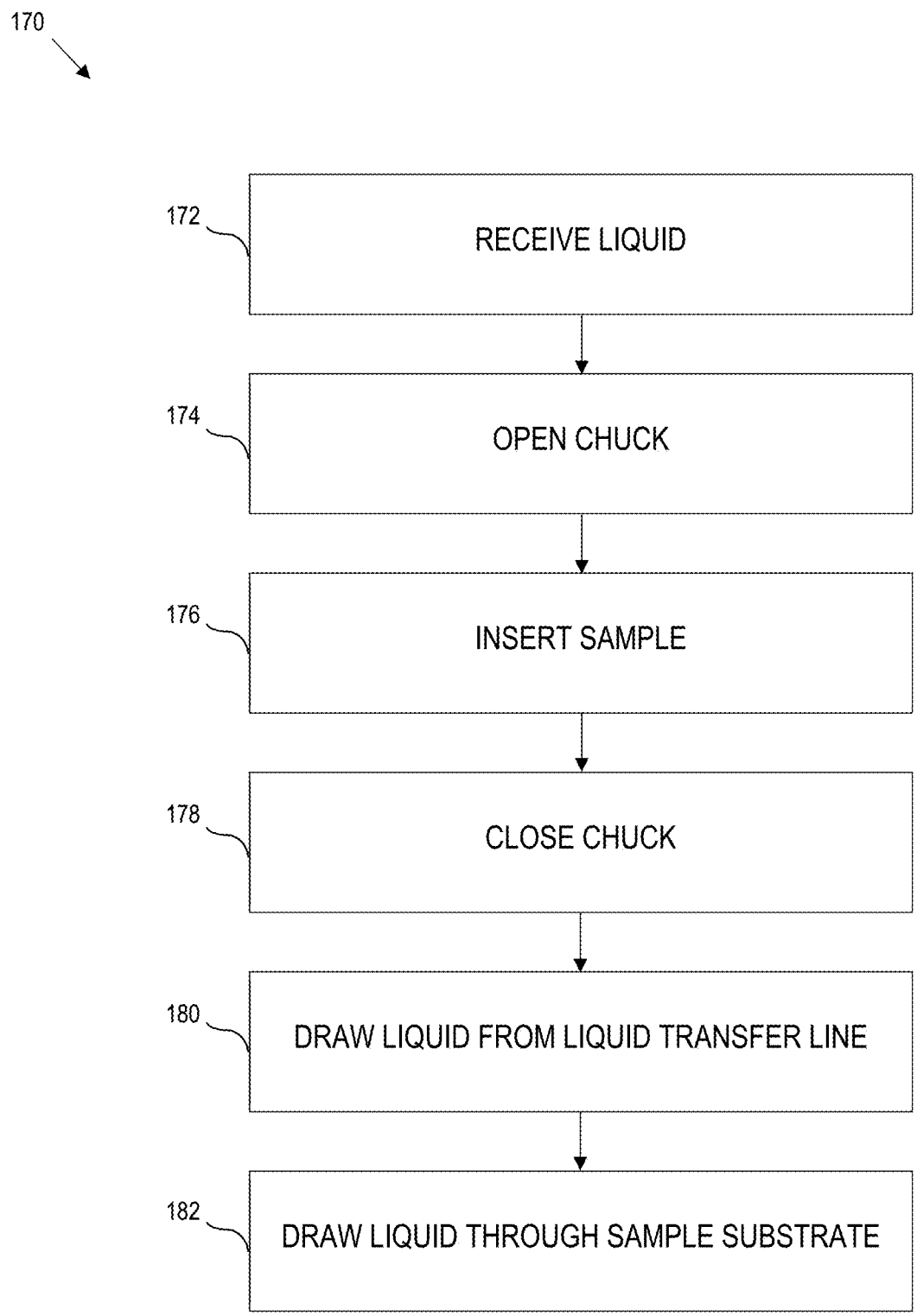
FIG. 5 is a flow chart of another process for preparing a sample according to aspects of the present disclosure.

Referring to FIG. 5, another process is illustrated for preparing a sample using a sample preparation system. As with the embodiment described with reference to FIG. 4, the process can be implemented as the sample preparation algorithm 122 executed by the controller 120 (FIG. 1 and FIG. 3). In this regard, the sample preparation system can include any combination of features described more fully herein.

The process 170 comprises receiving at 172, a liquid at a liquid transfer line, the liquid comprising suspended particles.

The process 170 further comprises opening, at 174 a chuck.

The process 170 yet further comprises inserting, at 176, a sample substrate between the chuck and the liquid transfer line, the sample substrate comprising a surface.

The process 170 still further comprises closing, at 178 the chuck.

The process 170 additionally comprises drawing, at 180, the liquid from the liquid transfer line through a capillary tube, the capillary tube being located within a support tube.

The process 170 moreover, comprises drawing, at 182, the liquid through the sample substrate such that particles are trapped on the surface of the sample substrate.

In some embodiments, the process 170 can further comprise generating a vacuum using a pump, the generated vacuum creating a vacuum seal between the chuck and the support tube, drawing a predetermined volume of the liquid through the sample substrate using the generated vacuum, deactivating the vacuum, and opening the chuck to enable removal of the sample substrate.

In some embodiments, inserting the sample substrate comprises inserting a flexible and pliable substrate that avoids substantially interfering with the vacuum seal. In other embodiments, inserting the sample substrate comprises inserting a puncturable substrate to create a registration feature. The registration feature can be used for positioning collected particles on the puncturable substrate for subsequent optical analysis. In yet other embodiments, inserting the sample substrate comprises inserting a substrate with a metallic coating, the metallic coating creating an optically reflective surface on the substrate, where the optically reflective surface permits measurement of the particles by an optical system, and the metallic coating is substantially unmeasurable by the optical spectrum. In still other embodiments, inserting the sample substrate comprises inserting an advanceable strip, the advanceable strip for collecting successive samples.

Although described herein with regard to FIG. 1 through FIG. 5, a sample preparation system can be configured to include any combination of components, features, and capabilities described herein, including drawing from select aspects across on or more figures.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description but is not intended to be exhaustive or limited to the disclosure in the form disclosed. Many modifications and variations will be apparent to those of ordinary skill in the art without departing from the scope and spirit of the disclosure. Aspects of the disclosure were chosen and described in order to best explain the principles of the disclosure and the practical application, and to enable others of ordinary skill in the art to understand the disclosure for various embodiments with various modifications as are suited to the particular use contemplated.

What is claimed is:

1. A sample preparation system, comprising:
   a capillary tube having a discharge end;
   a liquid transfer line that terminates into the capillary tube, wherein:
      the liquid transfer line receives a liquid comprising suspended particles; and
      transfers the received liquid to the capillary tube;
   a support tube having a discharge end, the support tube positioned about the capillary tube such that the discharge end of the capillary tube is spaced from and receded into the discharge end of the support tube;
   a sample substrate positionable adjacent to the support tube, wherein:
      the sample substrate receives the liquid discharged from the capillary tube;
      the sample substrate filters the suspended particles from the liquid;
   a chuck interposed between a support member and the sample substrate, the chuck operable to open and close, thereby selectively creating a seal between the sample substrate and the support tube; and
   a pump that draws the liquid through the sample substrate.

2. The sample preparation system according to claim 1, wherein the capillary tube comprises an opening having a length and a width such that the width is orthogonal to the length, and the length is greater than the width.

3. The sample preparation system according to claim 2, wherein the length is greater than one (1) millimeter (mm).

4. The sample preparation system according to claim 2, wherein the width is between one (1) micrometer (μm) and one (1) millimeter (mm).

5. The sample preparation system according to claim 1 further comprising a securement that secures the capillary tube within the support tube, the support tube being airtight except at a designated position.

6. The sample preparation system according to claim 5, wherein the securement comprises a removeable fixture.

7. The sample preparation system according to claim 1, wherein the sample substrate comprises a porous filter that prohibits targeted particles from passing through the porous filter, where the porous filter further permits passage of liquid and air through the porous filter.

8. The sample preparation system according to claim 1, wherein the sample substrate comprises a registration feature that allows registration of the sample substrate relative to the capillary tube.

9. The sample preparation system according to claim 1, wherein the sample substrate comprises a surface coating that collects particles of interest thereon, the particles of interest measurable on an optical spectrum.

10. The sample preparation system according to claim 9, wherein the surface coating of the sample substrate comprises a metallic coating that is optically reflective, the metallic coating further substantially unmeasurable on the optical spectrum.

11. The sample preparation system according to claim 1, wherein the sample substrate comprises a strip of material that provides for multiple, discrete, and individual sample collection sites.

12. The sample preparation system according to claim 1, wherein the pump exhausts portions of the liquid that are not retained on the sample substrate.

13. A process for preparing a sample using a sample preparation system, the process comprising:
   receiving a liquid at a liquid transfer line, the liquid comprising suspended particles;
   opening a chuck;
   inserting a sample substrate between the chuck and the liquid transfer line, the sample substrate comprising a surface;
   closing the chuck;
   drawing the liquid from the liquid transfer line through a capillary tube, the capillary tube being located within a support tube; and
   drawing the liquid through the sample substrate such that particles are trapped on the surface of the sample substrate.

14. The process for claim 13 further comprising:
   generating a vacuum using a pump, the generated vacuum creating a vacuum seal between the chuck and the support tube;
   drawing a predetermined volume of the liquid through the sample substrate using the generated vacuum;
   deactivating the vacuum; and
   opening the chuck to enable removal of the sample substrate.

15. The process for claim 14, wherein inserting the sample substrate comprises:
   inserting a flexible and pliable substrate that avoids substantially interfering with the vacuum seal.

16. The process for claim 13, wherein inserting the sample substrate comprises:
   inserting a puncturable substrate to create a registration feature, the registration feature for positioning collected particles on the puncturable substrate for subsequent optical analysis.

17. The process for claim 13, wherein inserting the sample substrate comprises:
   inserting a substrate with a metallic coating, the metallic coating creating an optically reflective surface on the substrate, the optically reflective surface permitting measurement of the particles by an optical system, the metallic coating being substantially unmeasurable by the optical spectrum.

18. The process for claim 13, wherein inserting the sample substrate comprises:
   inserting an advanceable strip, the advanceable strip for collecting successive samples.

19. A sample preparation system, comprising:
   a capillary tube having a discharge end and an opening, wherein the opening has a length and a width such that the width is orthogonal to the length, and the length is greater than the width;
   a liquid transfer line that terminates into the capillary tube, wherein:
      the liquid transfer line receives a liquid comprising suspended particles; and
      transfers the received liquid to the capillary tube;
   a support tube having a discharge end, the support tube positioned about the capillary tube such that the discharge end of the capillary tube is spaced from and receded into the discharge end of the support tube;
   a securement that secures the capillary tube within the support tube, the support tube airtight except at a designated position;
   a sample substrate positionable adjacent to the support tube, wherein:
      the sample substrate receives the liquid discharged from the capillary tube;
      the sample substrate filters the suspended particles from the liquid;
   a chuck interposed between a support member and the sample substrate, the chuck operable to open and close, thereby selectively creating a seal between the sample substrate and the support tube; and
   a pump that draws the liquid through the sample substrate and that exhausts portions of the liquid that are not retained on the sample substrate.

20. The sample preparation system according to claim 19, wherein the sample substrate comprises:
   a porous filter that prohibits targeted particles from passing through the porous filter, where the porous filter further permits passage of liquid and air through the porous filter;
   a registration feature that allows registration of the sample substrate relative to the capillary tube; and
   a surface coating that collects particles of interest thereon, the particles of interest measurable on an optical spectrum.

* * * * *